(12) United States Patent
Nieman et al.

(10) Patent No.: US 6,288,118 B1
(45) Date of Patent: Sep. 11, 2001

(54) THERAPIES FOR TREATING PULMONARY DISEASES

(75) Inventors: Richard Nieman, Philadelphia; Anthony S Rebuck, Collegeville; Theodore J Torphy, Bryn Mawr, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/763,516
(22) PCT Filed: Aug. 24, 1999
(86) PCT No.: PCT/US99/19332
§ 371 Date: Feb. 23, 2001
§ 102(e) Date: Feb. 23, 2001
(87) PCT Pub. No.: WO00/12078
PCT Pub. Date: Mar. 9, 2000

Related U.S. Application Data

(60) Provisional application No. 60/097,973, filed on Aug. 26, 1998.

(51) Int. Cl.$^7$ .......................... A61K 31/19; A61K 31/135
(52) U.S. Cl. ............................................ 514/572; 514/653
(58) Field of Search ...................................... 514/572, 653

(56) References Cited

U.S. PATENT DOCUMENTS

| 5,858,694 | 1/1999 | Plazza et al. . |
| 5,889,003 | 3/1999 | Dhainaut et al. . |
| 5,919,801 | 7/1999 | Dhalnaut et al. . |

*Primary Examiner*—Raymond Henley, III
(74) *Attorney, Agent, or Firm*—James M. Kanagy; Charles M. Kinzig

(57) ABSTRACT

This invention relates to treating pulmonary diseases such as chronic obstructive pulmonary disease or asthma by administering a phosphodiesterase-4 inhibitor with a beta-adrenergic bronchodilator.

4 Claims, No Drawings

THERAPIES FOR TREATING PULMONARY DISEASES

This is a 371 of PCT/US 99/19332 filed Aug. 24, 1999 which claims priority to U.S. Provisional Application No. 60/097,973 filed Aug. 26, 1998.

AREA OF THE INVENTION

This invention relates compositions and methods for preventing or reducing the onset of symptoms of pulmonary diseases, or treating or reducing the severity of pulmonary diseases. In particular it relates to compositions and methods for treating pulmonary diseases mediated by phosphodiesterase 4 (PDE4) by administering a PDE4 inhibitor with other pharmaceutically active agents which affect pulmonary function.

BACKGROUND OF THE INVENTION

Identification of novel therapeutic agents for treating pulmonary diseases is made difficult by the fact that multiple mediators are responsible for the development of the disease. Thus, it seems unlikely that eliminating the effects of a single mediator could have a substantial effect on all three components of chronic asthma. An alternative to the "mediator approach" is to regulate the activity of the cells responsible for the pathophysiology of the disease.

One such way is by elevating levels of cAMP (adenosine cyclic 3',5'-monophosphate). Cyclic AMP has been shown to be a second messenger mediating the biologic responses to a wide range of hormones, neurotransmitters and drugs; [Krebs Endocrinology Proceedings of the 4th International Congress Excerpta Medica, 17–29, 1973]. When the appropriate agonist binds to specific cell surface receptors, adenylate cyclase is activated, which converts $Mg^{+2}$-ATP to cAMP at an accelerated rate.

Cyclic AMP modulates the activity of most, if not all, of the cells that contribute to the pathophysiology of extrinsic (allergic) asthma. As such, an elevation of cAMP would produce beneficial effects including: 1) airway smooth muscle relaxation, 2) inhibition of mast cell mediator release, 3) suppression of neutrophil degranulation, 4) inhibition of basophil degranulation, and 5) inhibition of monocyte and macrophage activation. Hence, compounds that activate adenylate cyclase or inhibit phosphodiesterase should be effective in suppressing the inappropriate activation of airway smooth muscle and a wide variety of inflammatory cells. The principal cellular mechanism for the inactivation of cAMP is hydrolysis of the 3'-phosphodiester bond by one or more of a family of isozymes referred to as cyclic nucleotide phosphodiesterases (PDEs).

It has been shown that a distinct cyclic nucleotide phosphodiesterase (PDE) isozyme, PDE IV, is responsible for cAMP breakdown in airway smooth muscle and inflammatory cells. [Torphy, "Phosphodiesterase Isozymes: Potential Targets for Novel Anti-asthmatic Agents" in New Drugs for Asthma, Barnes, ed. IBC Technical Services Ltd., 1989]. Research indicates that inhibition of this enzyme not only produces airway smooth muscle relaxation, but also suppresses degranulation of mast cells, basophils and neutrophils along with inhibiting the activation of monocytes and neutrophils. Moreover, the beneficial effects of PDE IV inhibitors are markedly potentiated when adenylate cyclase activity of target cells is elevated by appropriate hormones or autocoids, as would be the case in vivo. Thus PDE IV inhibitors would be effective in the lung, where levels of prostaglandin $E_2$ and prostacyclin (activators of adenylate cyclase) are elevated. Such compounds would offer a unique approach toward the pharmacotherapy of bronchial asthma and possess significant therapeutic advantages over agents currently on the market.

In addition, it could be useful to combine therapies in light of the fact that the etiology of many pulmonary diseases involves multiple mediators. In this invention there is presented the combination of a PDE 4 inhibitor and an inhaled long-acting beta agonist for treating pulmonary diseases, particularly COPD or asthma.

SUMMARY OF THE INVENTION

In a first aspect this invention relates to a method for treating a pulmonary disease by administering to a patient in need thereof an effective amount of a PDE 4 inhibitor and a long-acting beta adrenergic bronchodilator either in a single combined form, separately, or separately and sequentially where the sequential administration is close in time, or remote in time.

In a second aspect this invention relates to a composition for treating a pulmonary disease comprising an effective amount of a PDE4 inhibitor, an effective amount of a long-acting beta adrenergic bronchodilator and a pharmaceutically acceptable excipient.

In a third aspect this invention relates to a method for preparing a composition which is effective for preventing the symptoms of treating a pulmonary disease which method comprises mixing an effective amount of a PDE4 inhibitor and a long-acting beta adrenergic bronchodilator with a pharmaceutically acceptable excipient.

DETAILED DESCRIPTION OF THE INVENTION

The combination therapy contemplated by this invention comprises administering a PDE4 inhibitor with a long-acting beta adrenergic bronchodilator to prevent onset of a pulmonary disease event or to treat an existing condition. The compounds may be administered together in a single dosage form. Or they may be administered in different dosage forms. They may be administered at the same time. Or they may be administered either close in time or remotely, such as where one drug is administered in the morning and the second drug is administered in the evening. The combination may be used prophylactically or after the onset of symptoms has occurred. In some instances the combination(s) may be used to prevent the progression of a pulmonary disease or to arrest the decline of a function such as lung function.

The PDE4 inhibitor useful in this invention may be any compound that is known to inhibit the PDE4 enzyme or which is discovered to act in as PDE4 inhibitor, and which are only PDE4 inhibitors, not compounds which inhibit other members of the PDE family as well as PDE4. Generally it is preferred to use a PDE4 antagonists which has an $IC_{50}$ ratio of about 0.1 or greater as regards the $IC_{50}$ for the PDE IV catalytic form which binds rolipram with a high affinity divided by the $IC_{50}$ for the form which binds rolipram with a low affinity.

PDE inhibitors used in treating inflammation and as bronchodilators, drugs like theophylline and pentoxyfyllin, inhibit PDE isozymes indiscriminently in all tissues. These compounds exhibit side effects, apparently because they non-selectively inhibit all 5 PDE isozyme classes in all tissues. The targeted disease state may be effectively treated by such compounds, but unwanted secondary effects may be exhibited which, if they could be avoided or minimized, would increase the overall therapeutic effect of this approach to treating certain disease states. For example, clinical studies with the selective PDE 4 inhibitor rolipram, which was being developed as an antidepressant, indicate it has psychotropic activity and produces gastrointestinal effects, e.g., pyrosis, nausea and emesis.

It turns out that there are at least two binding forms on human monocyte recombinant PDE 4(hPDE 4) at which inhibitors bind. One explanation for these observations is that hPDE 4exists in two distinct forms. One binds the likes of rolipram and denbufylline with a high affinity while the other binds these compounds with a low affinity. The preferred PDE4 inhibitors of for use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an $IC_{50}$ ratio of about 0.1 or greater as regards the $IC_{50}$ for the PDE 4catalytic form which binds rolipram with a high affinity divided by the $IC_{50}$ for the form which binds rolipram with a low affinity. Examples of such compounds are:

Papaverine—1-[(3,4-dimethoxyphenyl )methyl]-6,7-dimethoxyisoquinoline;

Trequinsin—2,3,6,7-tetrahydro-2-(mesitylimino)-9,10-dimethoxy-3-methyl-4H-primido[6,1-α]isoquinoline-4-one;

Dipyrimadole—the generic name for 2,2',2",2'"-[(4,8-dipiperldinopyrimido[5,4-d]pyrimidine-2-6-diyl)dinitrilo]tetraethanol;

(R)-(+)-1-(4-bromobenzyl)-4-[(3-cyclopentyloxy)-4-methoxyphenyl]-2pyrrolidone;

(R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N2-cyano-S-methyl-isothioureido]benzyl)-2-pyrrolidone, cis-[4-cyano-4-(3-cyclopentyloxy-4-methoxyphenyl)cyclohexan-1-carboxylate];

cis-[4-cyano-4-(3-cyclopropylmethoxy-4-difluoromethoxyphenyl)cyclohexan-1-ol];

(R)-(+)-ethyl [4-(3-cyclopentyloxy-4-methoxyphenyl)pyrrolidine-2-ylidene]acetate;

(S)-(−)-ethyl [4-(3-cyclopentyloxy-4-methoxyphenyl)pyrrolidine-2-ylidene]acetate, Most preferred are those PDE4 inhibitors which have an $IC_{50}$ ratio of greater than 0.5, and particularly those compounds having a ratio of greater than 1.0. Preferred compounds are trequinsin, dipyridamole, and papaverine. Compounds such as cis-[cyano-4-(3-cyclopentyloxy-4-methoxyphenyl)cyclohexan-1-carboxylate], 2-carbomethoxy-4-cyano-4-(3cyclopropylmethoxy-4-diflouromethoxyphenyl)cyclohexan-1-one, and cis-[4-cyano-4-(3-cyclopropylmethoxy-4-difluoromethoxyphenyl)cyclohexan-1-ol] are examples of structures which bind preferentially to the low affinity binding site and which have an $IC_{50}$ ratio of 0.1 or greater.

Reference is made to co-pending U.S. application Ser. No. 08/456,274 filed May 31, 1995 and its parent a PCT application published Jan. 05, 1995 as W)95/00139 for a methods and techniques which can be used to identify compound which have a high/low $IC_{50}$ ratio of 0.1 or greater as referred to in the proceeding paragraph. This co-pending application, U.S. Ser. No. 08/456,274 is incorporated herein by reference as if set out in full herein.

The several specific compounds set out above which do not have a generic or trade name can be made by the processed described in co-pending U.S. patent applications U.S. Ser. No. 862,083 filed Oct. 30, 1992; U.S. Ser. No. 862,111 filed Oct. 30, 1992; U.S. Ser. No. 862,030 filed Oct. 30, 1992; and U.S. Ser. No. 862,114 filed Oct. 30, 1992 or their progeny or U.S. patent(s) claiming priority from one or more of these applications. Each of these applications or related patents is incorporated herein by preference in full as if se t out in this document.

The beta adrenergic bronchodilator, $\beta_2$-adreneric agonists really, used in this invention will be a long-acting compound. Any compound of this type can be used in this combination therapy approach. By long-lasting it is meant that the drug will have an affect on the bronchi that lasts around 6 hours or more, up to 12 hours in some instances. To illustrate, certain resorcinols such as metaproterenol, terbutaline, and fenoterol can be combined with a PDE4 inhibitor in the practice of this invention. Further examples of useful beta adrenergic bronchodilators is the likes of two structurally related compounds, albuterol {racemic ( $^1$-[(t-butylamino)methyl]-4-hydroxy-m-xylene-, '-diol)} and formoterol {(R*, R*)-(±)-N-[2-hydroxy-5-[1-hydroxy-2-[[2-(4-methoxyphenyl)-1-methylethyl]ethyl]phenyl] formamide}.

Metaproterenol is the subject of U.S. Pat. No. 3,341,594 and is commercially available under the trade names of Alotec, Alupent, Metaprel or Novasmasol. Terbutaline is described in U.S. Pat. No. 3,938,838 and is available commercially as Brethine from Novartis. The preparation of fenoterol is described in U.S. Pat. No. 4,341,593. It is sold under several trade names, including Airum, Berotec, Dosberotec and Partusisten. Albuterol is sold under the trademark Proventil® by Schering Corporation. Formoterol is described in U.S. Pat. No. 3,994,974 and is available commercially under the names Atock and Foradil.

A preferred combination therapy is that of formoterol and cis-[cyano-4-(3-cyclopentyloxy-4-methoxyphenyl) cyclohexan-1-carboxylate].

These drugs, the beta agonists, are usually administered as an oral or nasal spray or aerosol, or as an inhaled powder. Usually these drugs are not administered systemically or by injection. The PDE4 inhibitors can be administered orally or by inhalation (orally or internasally). This invention contemplates either co-administering both drugs in one delivery form such as an inhaler, that is putting both drugs in the same inhaler. Alternatively one can put the PDE4 inhibitor into pills and package them with an inhaler that contains the beta agonist. Formulations are within the skill of the art.

It is contemplated that both active agents would be administered at the same time, or very close in time. Alternatively, one drug could be taken in the morning and one later in the day. Or in another scenario, one drug could be taken twice daily and the other once daily, either at the same time as one of the twice-a-day dosing occurred, or separately. Preferably both drugs would be taken together at the same time.

The foregoing statements and examples are intended to illustrate the invention, not to limit it. Reference is made to the claims for what is reserved to the inventors hereunder.

What is claimed is:

1. A composition for treating a pulmonary disease comprising an effective amount of a PDE4 inhibitor, an effective amount of a long-acting beta adrenergic bronchodilator and a pharmaceutically acceptable excipient.

2. A method for preparing a composition which is effective for preventing the symptoms of, or treating a pulmonary disease which method comprises mixing an effective amount of a PDE4 inhibitor and a long-acting beta adrenergic bronchodilator with a pharmaceutically acceptable excipient.

3. A method for treating a pulmonary disease by administering to a patient in need thereof an effective amount of a PDE 4inhibitor and a long-acting beta adrenergic bronchodilator either in a combined form, separately, or separately and sequentially where the sequential administration is close in time or remote in time.

4. The method of claim 3 wherein the PDE4 inhibitor is cis-[4-cyano-4-(3-cyclopentyloxy-4-methoxyphenyl) cyclohexan-1-carboxylate] and the beta agonist is formoterol.

* * * * *